United States Patent Office

Plant Pat. 1,488
Patented June 26, 1956

1,488

PURPLE VERBENA PLANT

Florence Clyde Chandler, Ardsley, N. Y., assignor to Boyce Thompson Institute for Plant Research, Inc., Yonkers, N. Y., a corporation of New York No Drawing. Application July 18, 1955, Serial No. 522,889

1 Claim. (Cl. 47—60)

This invention provides a new and distinct variety of purple verbena plant. The new variety of plant is particularly characterized by its unique purple flowers which are exceptionally large forming large clusters of many flowers which are borne on long stiff stems, by large dark green leaves, by erect habit, and by good vigor. The new variety has been produced asexually from cuttings and the characteristics appear to be fixed.

The distinct variety of purple verbena was produced by selecting a purple flowered plant growing in a bed of mixed verbena seedlings and propagating it vegetatively. Growing tips of the branches of this selected seedling were treated with colchicine. The tips which were affected by the colchicine were removed and rooted in sand. The resulting plants produced no seed to fully controlled self or close pollinations. Chromosome studies reveal that this selected plant so produced is a tetraploid with $2n=20$ chromosomes.

The new variety of plants as thus originated were asexually reproduced from cuttings at Boyce Thompson Institute for Plant Research, Inc., Yonkers, New York.

In my Plant Pat. 1,333, issued December 21, 1954, the drawing illustrates a plant having the identical appearance of the plants of this invention.

*Flowers*

The individual flowers are about one inch in diameter and according to Ridgway are between prune purple and fluorite purple. The nearest color according to Munsell is P 3/8 (purple hue, 3 value, and 8 chroma). The freshly opened flowers have a marked white eye which extends from the center of the corolla to the point of union of the petals which produces a star-like appearance. The white area disappears in older flowers which are uniformly purple. The flower clusters are relatively large being about 2½ inches in diameter and 2¼ inches long in the flower axis, and generally consist of from 40 to 50 flowers. The clusters are borne on stiff, upright stems about 14 inches long, about ⅛ inch in diameter, and the clusters are usually about 12 inches above the ground.

*Leaves*

The leaves are dark green, thick, about 2 inches in diameter, and 2¾ inches in length near the base while the leaves at the tips of the branches are smaller, and they do not burn in the field during the summer months.

*Seeds*

This variety of plant has produced no seed to controlled self-pollinations and is propagated only by means of vegetative cuttings. The pollen is about 47% aborted and the grains are from 47 to 76 microns in diameter.

*General*

This new plant is more vigorous and robust than the old variety of Spectrum Red verbena. To many people the plant has noticeable but slight fragrance. The plant remains in good vegetative condition throughout the summer and the leaves remain green and do not burn during the summer. The plant flowers well and has a profusion of bloom throughout the summer and until killed by frost.

I claim:

The new and distinct variety of purple verbena plant substantially as illustrated in Plant Pat. 1,333 and described herein, characterized by large individual flowers which are uniformly purple in large clusters of many flowers borne on stiff, erect and long stems, by large deep green leaves, and by good vigor.

No references cited.